(12) United States Patent
Schmitt et al.

(10) Patent No.: US 10,335,255 B2
(45) Date of Patent: Jul. 2, 2019

(54) STRAW FOR THE PRESERVATION OF A PREDETERMINED DOSE OF LIQUID-BASED SUBSTANCE, IN PARTICULAR A BIOLOGICAL SUBSTANCE

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 147 days.

(21) Appl. No.: 15/120,575

(22) PCT Filed: Feb. 20, 2015

(86) PCT No.: PCT/FR2015/050411
§ 371 (c)(1),
(2) Date: Aug. 22, 2016

(87) PCT Pub. No.: WO2015/124875
PCT Pub. Date: Aug. 27, 2015

(65) Prior Publication Data
US 2017/0065390 A1    Mar. 9, 2017

(30) Foreign Application Priority Data
Feb. 21, 2014 (FR) .................... 14 51415

(51) Int. Cl.
*A61D 19/02* (2006.01)
*A01N 1/02* (2006.01)
*A61D 19/04* (2006.01)

(52) U.S. Cl.
CPC ......... *A61D 19/024* (2013.01); *A01N 1/0263* (2013.01); *A61D 19/04* (2013.01)

(58) Field of Classification Search
CPC ..... A61D 19/024; A61D 19/04; A01N 1/0263
(Continued)

(56) References Cited

U.S. PATENT DOCUMENTS 3,926,891 A * 12/1975 Gross .................... A61L 15/60
523/412
5,851,491 A    12/1998 Moulton
(Continued)

FOREIGN PATENT DOCUMENTS

EP      0873726 A1    10/1998
FR      995878 A      12/1951
(Continued)

OTHER PUBLICATIONS

Mozetič et al. Recent Progress in Surface Modification of Polyvinyl Chloride. Materials Dec. 18, 2012, 5, 2937-2959 (see attached).*

*Primary Examiner* — Navin Natnithithadha
*Assistant Examiner* — Sunita Reddy
(74) *Attorney, Agent, or Firm* — Browdy and Neimark, P.L.L.C.

(57) ABSTRACT

The invention relates to a straw comprising a tube (11) extending between a first end (13) and a second end (14) and comprising a stopper (12) placed in the tube near the first end thereof and extending between a first end (17) facing the first end of the tube, and a second end (20) facing the second end of the tube, said stopper and said tube being configured such that, after a liquid substance (22) has come in contact with the stopper via the second end thereof, the stopper blocks the passage of the liquid substance therethrough and is, by pushing on the first end thereof, slidable into the tube toward the second end thereof. Moreover, the stopper comprises, on the side of the second end of the tube, a barrier pad (16) consisting of hydrophobic threads over the entire cross-section of the tube.

15 Claims, 4 Drawing Sheets

(58) Field of Classification Search
USPC .............................. 600/33–35; 128/897–899
See application file for complete search history.

(56) References Cited

U.S. PATENT DOCUMENTS

| | | | |
|---|---|---|---|
| 5,868,178 A | 2/1999 | Lecointe | |
| 6,203,489 B1 | 3/2001 | Mori et al. | |
| 6,213,171 B1* | 4/2001 | Saint-Ramon | A61D 19/024 141/59 |
| 6,416,611 B1 | 7/2002 | Saint-Ramon et al. | |
| 7,252,988 B2* | 8/2007 | Saint-Ramon | A61D 19/024 220/364 |
| 7,837,611 B2* | 11/2010 | Ainley, Jr. | A61D 19/027 600/35 |
| 8,323,178 B2* | 12/2012 | Ainley, Jr. | A61D 19/027 600/35 |
| 9,918,464 B2* | 3/2018 | Schmitt | A61D 19/024 |
| 2001/0014376 A1* | 8/2001 | Saint-Ramon | A61D 19/024 428/36.9 |
| 2001/0029314 A1* | 10/2001 | Alferness | A61F 2/2481 600/37 |
| 2002/0183653 A1 | 12/2002 | Saint-Ramon et al. | |
| 2002/0188222 A1* | 12/2002 | Saint-Ramon | A61D 19/024 600/573 |
| 2006/0177352 A1 | 8/2006 | Ziegmann et al. | |
| 2009/0246782 A1* | 10/2009 | Kelso | B01L 3/502761 435/6.16 |
| 2015/0237848 A1 | 8/2015 | Schmitt | |

FOREIGN PATENT DOCUMENTS

| | | |
|---|---|---|
| FR | 2044797 A1 | 2/1971 |
| FR | 2651676 A1 | 3/1991 |
| FR | 2753367 A1 | 3/1998 |
| FR | 2771285 A1 | 5/1999 |
| FR | 2781662 A1 | 2/2000 |
| FR | 2784572 A1 | 4/2000 |
| FR | 2824255 A1 | 11/2002 |
| FR | 2824256 A1 | 11/2002 |
| GB | 669265 A | 4/1952 |
| WO | 2010070533 A1 | 6/2010 |

\* cited by examiner

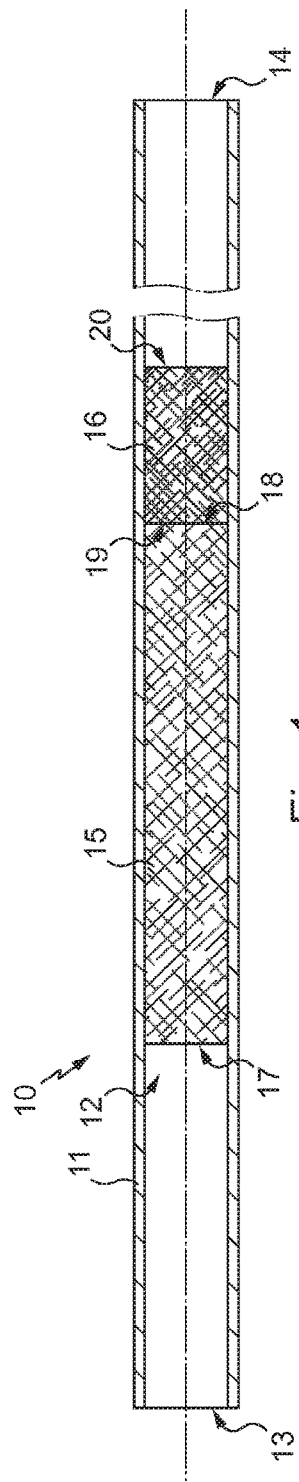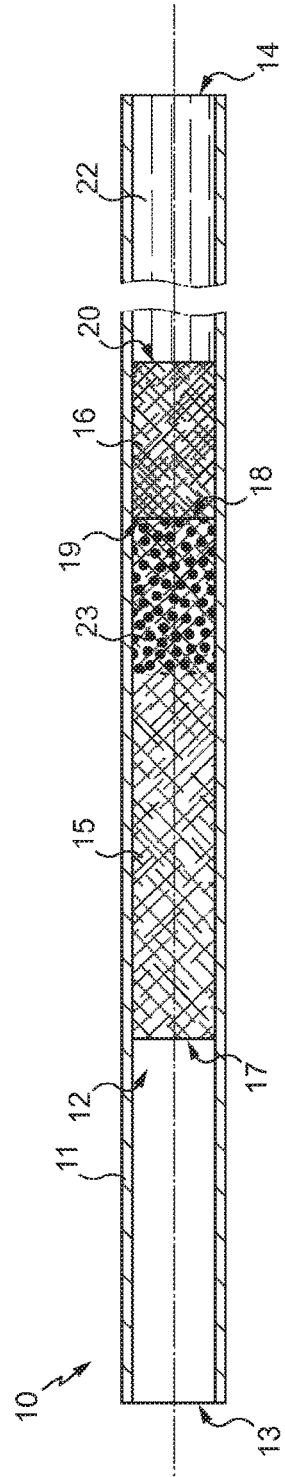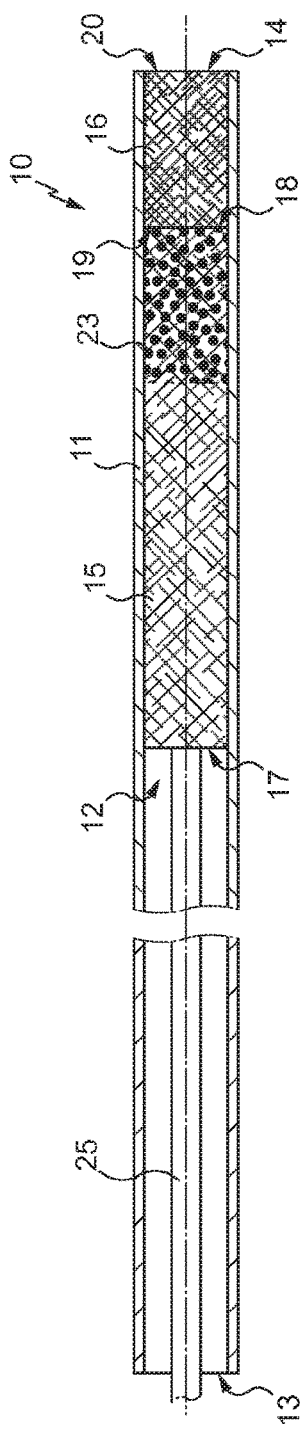

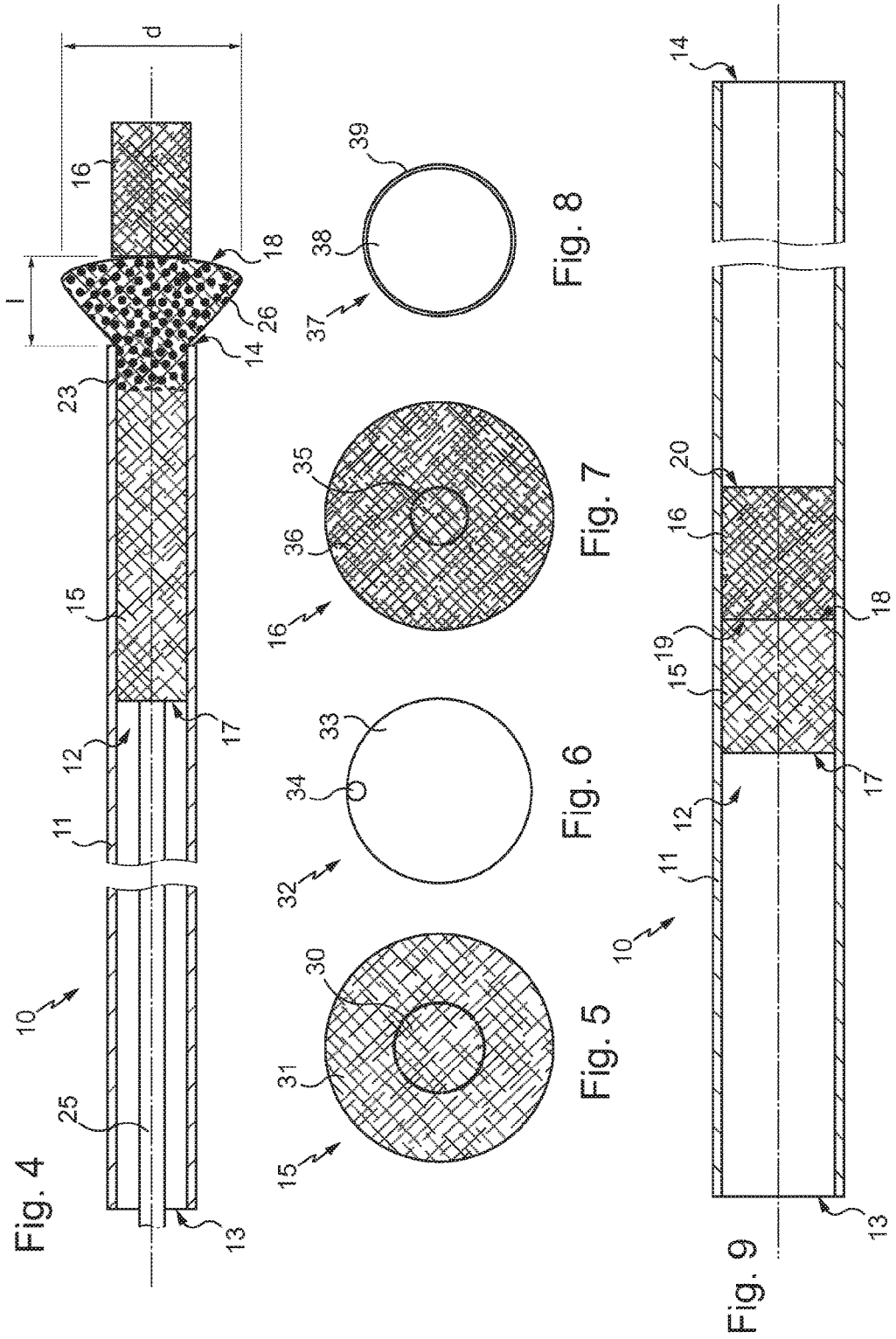

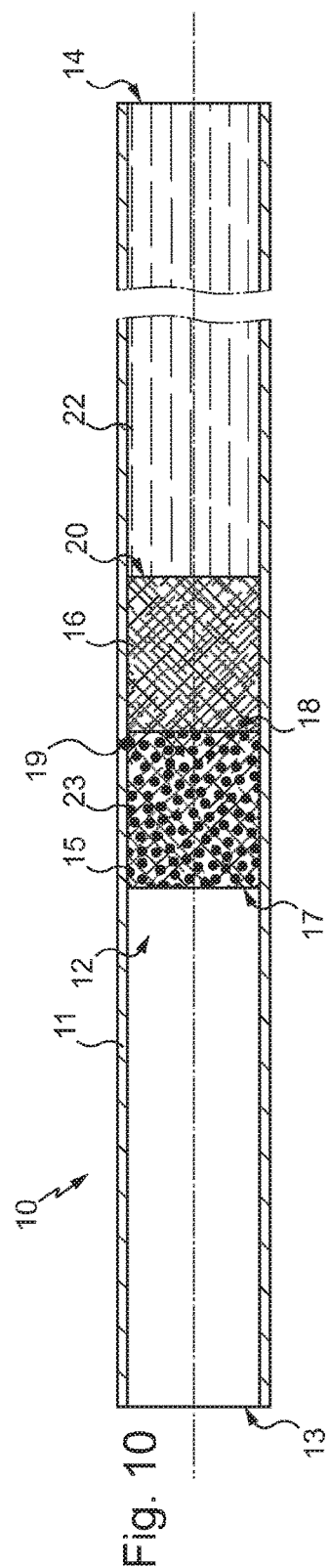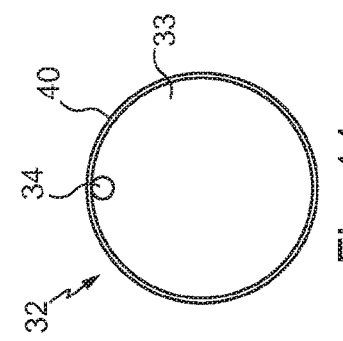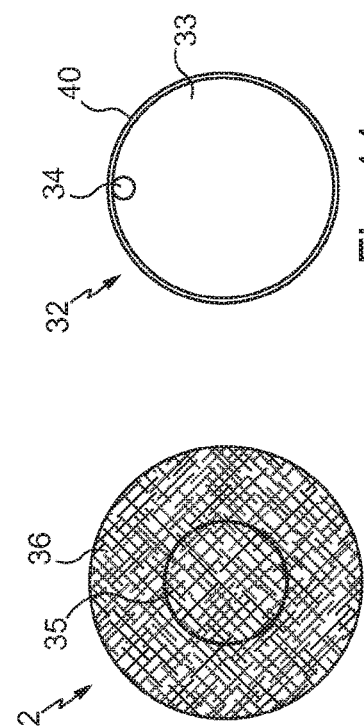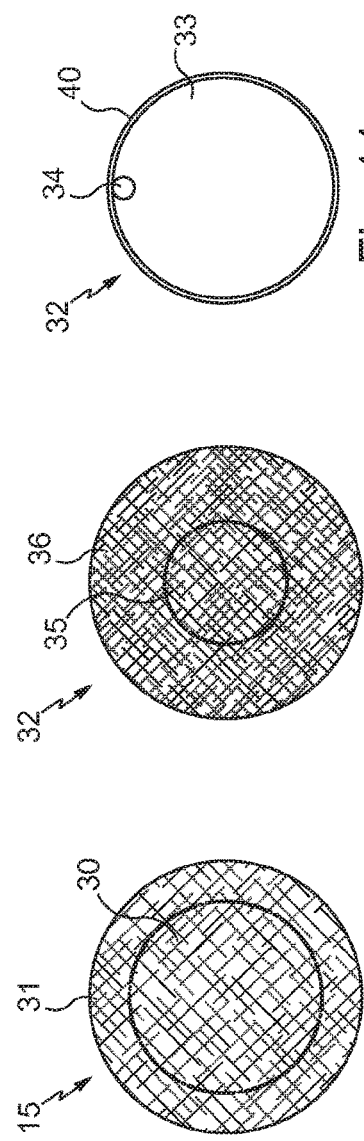

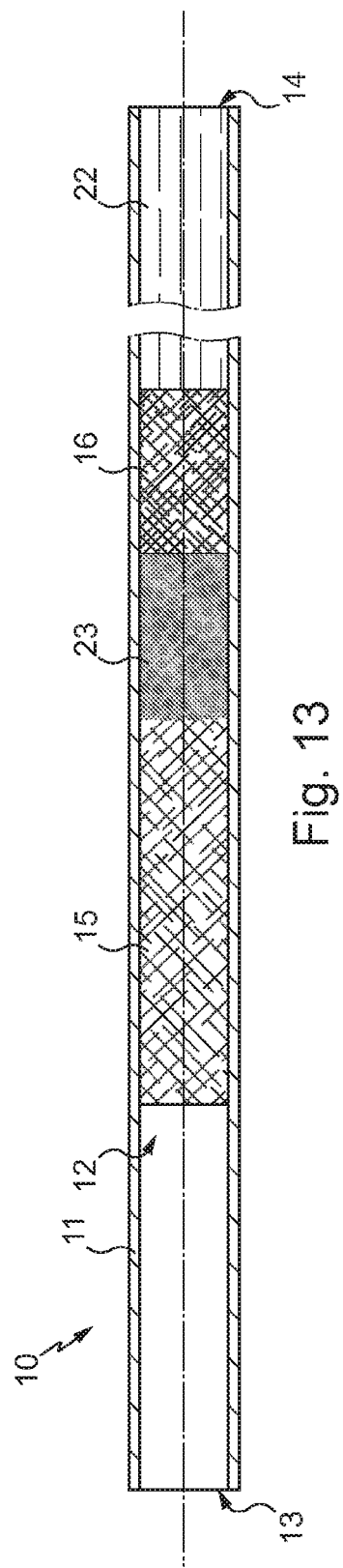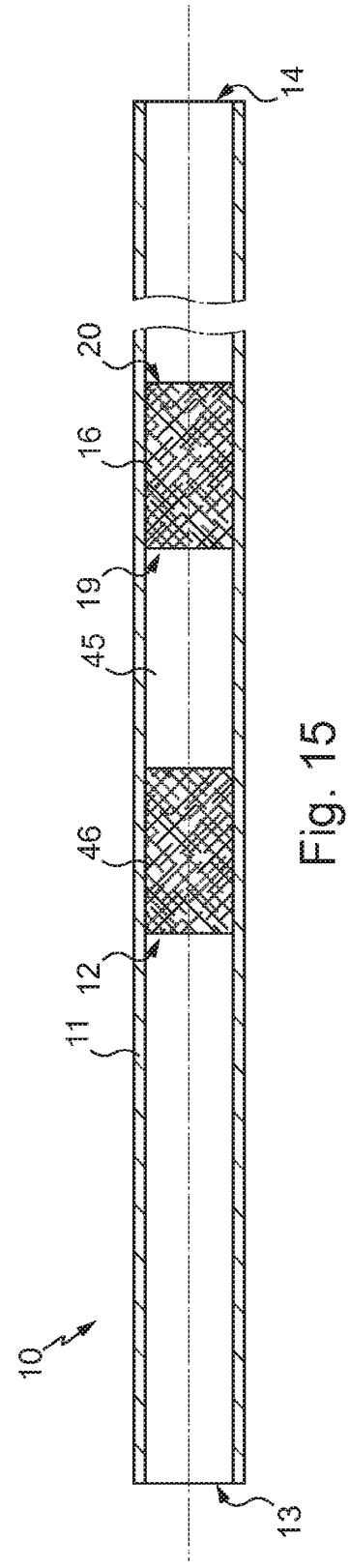

STRAW FOR THE PRESERVATION OF A PREDETERMINED DOSE OF LIQUID-BASED SUBSTANCE, IN PARTICULAR A BIOLOGICAL SUBSTANCE

The invention relates to straws for the storage of a predetermined dose of liquid-based substance, in particular a biological substance, for example pure or diluted animal semen or a storage medium containing embryos.

It is known that such a straw is conventionally formed by a thin tube, having for example an inner diameter of 1.6 or 2.5 mm, and by a stopper inserted in the thin tube.

In the filled state, the stopper is arranged close to a first end of the tube and the dose of substance is arranged in the straw between the stopper and the second end of the tube.

In order to fill the straw, the first end of the tube, close to the stopper, is placed in communication with a vacuum source, while the second end is placed in communication with a vessel containing the substance to be introduced into the straw. The air initially contained between the stopper and the second end is sucked through the stopper while the substance moves forward into the tube until it reaches the stopper, which it cannot pass because the stopper becomes liquid-tight.

If necessary, after filling, the straw is welded close to one or both of its ends and is stored cold.

In order to empty the straw, if necessary after cutting the welded end portions and thawing, a rod is inserted into the tube via the end closest to the stopper, until it bears against the stopper. Using this rod, the stopper is made to slide in the manner of a piston towards the end furthest from the stopper, so that the dose of substance initially contained in the straw is expelled through that end.

Straw stoppers are generally of the three-part type originally described in French patent 995.878, corresponding to British patent 669,265, i.e. formed by two plugs made from a fibrous substance enclosing a powder which, on contact with a liquid, is transformed into an impermeable paste or gel adhering to the wall of the tube so that the stopper is liquid-tight.

French patent application 2 651 676 proposes a stopper constituted by a first plurality of fibers and a second plurality of fibers associated together by braiding, the first plurality of fibers being constituted by fibers that can be polymerized under the action of the liquid and the second plurality of fibers being constituted by fibers that conduct liquid by capillary action. The fibers that can be polymerized under the action of the liquid are made from the same material as the powder of the conventional three-part stoppers.

French patent 2 753 367, to which U.S. Pat. No. 5,868,178 corresponds, proposes a three-part stopper in which the length of the outer plug is at least twice the length of the inner plug.

European patent application EP 0 873 726 proposes that the stopper is formed by a single-piece cylinder of hydrophobic microporous material. French patent applications 2 771 285 and 2 784 572, to which American patent application US 2001/0014376 and American patent U.S. Pat. No. 6,416,611 correspond, propose that the stopper is constituted by a stiff insert perforated by a substantially coaxial orifice and a hydrophobic microporous membrane associated with the insert in order to seal the insert orifice on the inside.

French patent application 2 781 662, to which American patent U.S. Pat. No. 6,203,489 corresponds, proposes that the stopper is constituted by a fibrous plug comprising a compound of gelling material present in a gas-permeable dispersed form and comprising a compound of support fibers, with the compound of gelling material being finely distributed throughout the compound of support fibers, so as to allow the swelling of the gelling material after it is brought into contact with a substance containing water, in order to form a stopper integrated with the compound of support fibers. The gelling material is made from the same material as the powder of the conventional three-part stoppers. The gelling material swells by absorbing the water present in the liquid in order to completely fill the tube, and then it reaches a state of gelation while binding with the compound of support fibers in order to form an integrated stopper.

French patent applications 2 824 255 and 2 824 256, to which American patent applications US 2002/0183653 and US 2002/0188222 correspond, propose to add to the stopper, besides the powder and fibers, non-absorbent elements, namely a core made from thermoplastic material, covered with a sleeve made from braided threads, and non-absorbent material in dispersed form, in the powder.

PCT application WO 2010/070533 proposes that the stopper is made as a single-piece cylinder of sintered self-sealing microporous material as described for example in PCT application WO 2010/070533, i.e. constituted by a microporous matrix and particles of a substance with a high capacity for water absorption supported by the microporous matrix, which provides the unit with an intrinsic mechanical coherence (the particles do not become detached) even in the dampened state.

The invention is directed to providing such a straw which is simple, convenient and economical to produce and which is efficient in use.

To that end the invention provides a straw for the preservation of a predetermined dose of liquid-based substance containing water, in particular a biological substance, comprising a tube extending between a first end and a second end and comprising a liquid-tight, gas-permeable stopper, which stopper being disposed in the tube close to its first end and extending between a first end turned towards the first end of the tube and a second end turned towards the second end of the tube, said stopper and said tube being configured so that after the liquid-based substance has come to meet the stopper by its second end, the stopper blocks the passage of the liquid-based substance and, by pushing on its first end, can be slid in the tube towards the second end of the tube;

characterized in that the stopper comprises towards the second end of the tube a barrier plug formed over the whole cross-section of the tube by hydrophobic threads.

On account of the fact that the fibers which form the barrier plug over the whole cross-section of the tube being hydrophobic, the plug has a repellant effect on water, and thus on the liquid-based substance containing water.

Although surprising, this repellant effect does not prevent the liquid-based substance from passing through the barrier plug and reaching the rest of the stopper, and in particular the sealing component which enables the stopper to be gas-permeable and liquid-tight.

This is because, in practice, the liquid-based substance, when it fills the tube of the straw, encounters the stopper with a certain speed. The effect of speed then dominates the repellant effect.

During the passage of the liquid-based substance within the barrier plug, the fibers of this plug, on account of being hydrophobic, do not absorb liquid.

After the sealing component of the stopper has become liquid-tight and the passage of the liquid-based substance has been blocked, the barrier plug does not keep the liquid situated in its interstices but returns it into the dose of liquid-based substance situated between the barrier plug and the second end of the tube.

As a result, there is no consumption, or very reduced consumption, of liquid-based substance by the barrier plug.

It will be noted that in the stoppers of straws that are already known and which employ a hydrophobic component, that hydrophobic component serves to block the passage of the liquid.

Here, the hydrophobic component in no way serves to block the passage of the liquid, and is on the contrary passed through by the liquid. It is only afterwards that it returns the liquid.

It will be noted that to recognize whether the barrier plug is hydrophobic, it suffices to remove it from the tube of the straw, in the initial dry state, and then to deposit drops of water on the barrier plug. If the barrier plug is hydrophobic, the drops run on the barrier plug without penetrating therein.

According to advantageous features of implementation of the straw according to the invention:
  each thread comprises fibers and a coating to make the thread hydrophobic, which coating comprises a fluorinated resin;
  said fluorinated resin is a fluorocarbon resin;
  said fluorocarbon resin has a formula $CF_3(CF_2)_n$ with n greater than 5 and preferably n=5 or n=7;
  said coating is polytetrafluoroethylene (PTFE);
  said stopper comprises, in addition to said barrier plug, a liquid-tight gas-permeable sealing component, with a first end of the barrier plug, turned towards the first end of the tube, and a second end of the sealing component, turned towards the second end of the tube, the the first end of the barrier plug and the second end of the sealing component (15) being disposed against each other;
  said sealing component is a swelling plug comprising a fibrous support agent and a swelling agent associated with the support agent, which swelling agent swells by absorption of water in contact with the liquid-based substance;
  said barrier plug extends between said first end and a second end forming the second end of the stopper;
  said swelling plug extends between a first end forming the first end of the stopper and said second end;
  the barrier plug is a braid formed by associating threads, and the swelling plug is a braid formed by associating threads, the barrier plug comprising more threads than the swelling plug;
  the swelling agent is a superabsorbent polymer configured to absorb several hundred times its volume of water;
  the swelling agent is sodium polyacrylate;
  the sealing component has a first predetermined color in the absence of prior contact with the liquid-based substance and a second predetermined color, having a hue different from the hue of the first color, when it has been in contact with said substance;
  the sealing component comprises a salt that is non-fluorophore in the dry state and fluorophore when it is dissolved in water; and/or
  the salt forms part of the group comprising a fluorescein salt, a Rhodamine B salt, a Rhodamine 6G salt and a salt of Eriochrome® Cyanine R.

The disclosure of the invention will now be continued with the description of embodiments, given below by way of non-limiting example, with reference to the attached drawings, in which:

FIG. 1 is a diagrammatic view in longitudinal cross-section of a straw according to the invention, in the empty state;

FIG. 2 is a view similar to FIG. 1 but showing the straw in the filled state;

FIG. 3 is a view similar to FIG. 2, but showing the straw after the dose of substance which was packaged therein has been expelled;

FIG. 4 is a view similar to FIG. 3, but showing the state assumed by the stopper when it has come partially out of the tube in a predetermined fashion;

FIG. 5 is a diagrammatic cross-section view of the swelling plug comprised by the stopper of the straw;

FIG. 6 is a diagrammatic cross-section view of one of the threads which form the swelling plug;

FIG. 7 is a diagrammatic cross-section view of the barrier plug comprised by the stopper of the straw;

FIG. 8 is a diagrammatic cross-section view of one of the threads which form the barrier plug;

FIGS. 9 to 12 are views similar to FIGS. 1, 2, 5 and 7 for a first variant of the straw according to the invention;

FIGS. 13 to 14 are views similar to FIGS. 2 and 6 for a second variant of the straw according to the invention; and FIG. 15 is a similar view to FIG. 1 for a third variant of the straw according to the invention.

The straw 10 illustrated in FIG. 1 comprises a tube 11 and a stopper 12.

The tube 11 is conventionally made from extruded plastic material, here transparent, with an inner diameter which is here of the order of 1.6 mm and a length of the order of 133 mm.

The outer diameter of the tube 11 is of the order of 2 mm.

The tube 11 extends between an end 13 and an end 14.

The stopper 12 is formed by a swelling plug 15 and by a barrier plug 16.

The swelling plug 15 extends between an end 17 turned towards the end 13 of the tube 11 and an end 18 turned towards the end 14 of the tube 11.

The barrier plug 16 extends between an end 19 turned towards the end 13 of the tube 11 and an end 20 turned towards the end 14 of the tube 11.

The end 18 of the swelling plug 15 and the end 19 of the barrier plug 16 are arranged against each other.

The stopper 12 extends between the end 17 of the swelling plug 15 and the end 20 of the barrier plug 16.

As will be described below in more detail, the swelling plug 15 comprises a fibrous support agent and a swelling agent associated with the fibrous support agent, said swelling agent swells by absorption of water on contact with a liquid containing water, whereby the swelling plug 15 is gas-permeable and liquid-tight.

It will be noted that the swelling plug 15 is capable of performing the same function as the conventional three-part stopper, but that the production of the straw is simpler and more convenient as it is sufficient to insert the swelling plug 15 into the tube 11 (and not a first fibrous plug, then the gelling powder and then a second fibrous plug).

The barrier plug 16 is fibrous. It is gas-permeable and liquid-permeable.

In the initial state, shown in FIG. 1, the stopper 12 is disposed close to the end 13 of the tube 11 and it is provided such that in the filled state, the dose of liquid substance 22 (FIG. 2) which must be preserved in the straw 10 is disposed between the stopper 12 and the end 14 of the tube 11 that is the furthest from the stopper 12. The substance 22 is liquid-based and contains water.

In order to fill the straw 10, the end 13 is placed in communication with a vacuum source while the end 14 is placed in communication with a vessel containing the substance 22 to be introduced into the straw.

The air initially contained between the stopper 12 and the end 14 is sucked through the stopper 12 while the substance 22 moves forward in the tube 11 until it comes up against the stopper 12, via the end 20 of the barrier plug 16 turned towards the end 14 of the tube 11, i.e. via the end of the stopper 12 shown on the right in FIGS. 1 and 2.

The substance 22 passes through the barrier plug 16 and comes up against the swelling plug 15 via its end 18 turned towards the end 14 of the tube 11, i.e. via the end shown on the right in FIGS. 1 and 2.

On contact with the substance 22, an area 23 of the swelling plug 15 situated close to its end 18 assumes a state of swelling constrained by the tube 11 which blocks the passage of the substance 22.

The straw 10 is then in the filled state shown in FIG. 2.

It will be observed that the area 23 of swelling constrained by the plug 15 is relatively short, here of the order of 3 mm starting from the end 18.

It is in fact found that the swelling dynamics of the swelling plug 15 on contact with the liquid-based substance 22 is such that a state of constrained swelling that is sufficient to block the passage of the liquid is reached when the swelling takes place only over a relatively short distance starting from the end 18, here of the order of 3 mm.

Albeit surprisingly, using a swelling agent with fast swelling dynamics, i.e. capable of absorbing a large quantity of liquid very rapidly, does not result in the swelling plug 15 absorbing a large quantity of the liquid-based substance 22, but on the contrary, given the speed with which is reached the state of constrained swelling allowing the passage of the liquid to be blocked, the quantity of liquid absorbed is relatively moderate, for example of the order of 3% of the dose of substance 22 introduced into the straw 10.

It will be noted that the state of swelling constrained by the tube 11, assumed by the swelling plug 15, results in the swelling plug 15 being maintained relatively firmly in position with respect to the tube 11 of the straw 10.

In particular, the plug 15 can be maintained during handling of the straw 10 in the filled state, and remain in place in the tube 11 during freezing of the substance 22.

If necessary, after filling, the straw is welded close to one or both of its ends 13 and 14 and is stored cold.

In order to empty the straw 10, if necessary after cutting off the welded end portions and thawing, a rod 25 (FIG. 3) is inserted into the tube 11, coming to rest against the end 17 of the swelling plug 15, i.e. against the end of the stopper 12 seen on the left in FIGS. 1 to 3.

Using this rod, the stopper 12 is made to slide in the manner of a piston towards the end 14, which causes the expulsion of the dose of substance 22 which had been introduced into the straw.

The end 14 is in the initial location or is set back with respect to the initial location if the tube 11 had been welded and the welded portion had been cut off before the expulsion of the dose of substance 22.

FIG. 3 shows the straw 10 at the end of the expulsion of the dose of substance 22. The end 20 of the barrier plug 16, which here forms the end of the stopper 12 turned towards the end 14 of the tube 11, is at the location of the end 14.

If the rod 25 is further pushed onto the stopper 12, the barrier plug 16 leaves the tube 11 then the swelling plug 15 in turn comes out of the tube 11.

In the configuration shown in FIG. 4, a part 26 of the swelling plug 15 has been removed from the tube 11. Here, length l of the portion 26 is of the order of 2 mm.

By providing that the part 26 of the swelling plug 15 that is out of the tube 11 has a length l comprised between 2 and 3 mm, it is ensured that the part 26 belongs entirely to the area 23 of constrained swelling, which has a length of the order of 3 mm.

As soon as it comes out of the tube 11, the part 26 is decompacted. Decompaction takes place because the tube 11 no longer takes up the tension arising from the fact that the swelling has been constrained. Due to the decompaction, the end 18 assumes a generally convex shape and the lateral surface of the part 26 assumes a generally frustoconical shape. This is how the part 26 expands. Once the expansion is complete, the end 18 has a contour which has here a diameter d of the order of 4 mm.

It will be noted that the part 26 of the swelling plug 15 is described above and is shown very diagrammatically in FIG. 4. Due to the fact that the part 26 of the swelling plug 15 is decompacted, its actual contour displays irregularities around the general contour described and shown.

In practice, the configuration shown in FIG. 4 can be obtained by placing the straw 10, after the latter has been emptied as shown in FIG. 3, on a horizontal surface and by pushing the stopper 12 until the swelling plug 15 has come out of the tube 11 over the length l from the end 18. In order to facilitate measurement of the length l, the horizontal surface is for example formed by a sheet of millimeter-squared paper.

Placing the straw 10 on the horizontal surface has no effect, or only a slight effect, on the shape assumed by the part 26, since the part 26 is decompacted after coming out of the tube 11.

As already stated, in the decompacted state assumed by the part 26, the swelling agent easily leaves the support agent.

If, starting from the configuration shown in FIG. 4, the straw 10 is rolled on the surface on which it rests, swelling agent is deposited on the surface as a result of the part 26 being rolled thereon.

The barrier plug 16 is useful in the straw 10 to ensure that the swelling agent in the dampened state remains in the swelling plug 15: the barrier plug 16 prevents it from passing towards the substance 22.

It will be noted that when the barrier plug 16 is in the tube 11, it is slightly compressed and that it therefore decompresses slightly when it is outside the tube 11 as shown in FIG. 4.

Here, the diameter of the barrier plug 16 outside the tube 11 is a few hundredths of a mm greater than the inner diameter of the tube 11.

The swelling plug 15 will now be described in detail, with reference to FIGS. 5 and 6.

The swelling plug 15 is a braid formed by associating threads 32 (FIG. 6). Here, the swelling plug 15 is formed by nineteen identical threads arranged in a core 30 and a cover 31 surrounding the core 30.

The core 30 is formed by three threads placed parallel, against one another.

The cover 31 has an annular cross section. It is formed by sixteen braided threads distributed in eight strands each comprising two threads.

One of the threads 32 which form the swelling plug 15 is shown very diagrammatically in cross section in FIG. 6.

The thread 32 comprises support fibers 33 and swelling fibers 34.

The support fibers 33 and the swelling fibers 34, in order to produce the thread 32, are assembled in a well-known manner by twist spinning.

Here, the support fibers 33 are discontinuous filaments of polyester and/or of viscose, neither cracked nor carded; and the swelling fibers 34 are discontinuous filaments of sodium polyacrylate, neither cracked nor carded.

Sodium polyacrylate is a superabsorbent polymer (SAP) capable of absorbing several hundred times its own volume of water.

It will be noted that sodium polyacrylate is not spermicidal and therefore is suitable for contact with animal semen.

The swelling fibers 34 here have a length of 6 mm at most.

The support fibers 33 are relatively aerated. This allows them to be gas-permeable.

Moreover, the aerated character of the support fibers 33 means that the thread 32 has a fluffy contour, which is favorable to maintaining the swelling plug 15 in the tube 11 when the straw is in the empty state (swelling plug 15 in the dry state).

The support fibers 33 occupy a relatively large volume in the thread 32 with respect to the volume occupied by the fibers 34, which are relatively compact.

This arrangement is favorable to the speed of absorption of liquid by the threads 32: The aerated character of the support fibers 33 and the large volume occupied by the support fibers 33 allow each thread 32 to be wetted by a large quantity of liquid and thus to feed the swelling fibers 34 very rapidly with liquid.

In the swelling plug 15 formed by associating threads 32 arranged as already indicated (core 30 and cover 31), the fibrous support agent is formed by the support fibers 33 of the threads 32 and the swelling agent is formed by the swelling fibers 34 of the threads 32.

As already indicated, if, starting from the configuration shown in FIG. 4, the straw 10 is rolled on the surface on which it rests, swelling agent is deposited on the surface as a result of the part 26 being rolled thereon.

In the swelling agent deposited on the surface, there are rod-shaped elements which are swelling fibers 34 that have absorbed a large quantity of liquid.

Here, in the dry state, the thread 32 comprises 75% support fibers 33 and 25% swelling fibers 34 by weight.

As a result, the swelling plug 15, in the dry state, comprises 75% fibrous support agent and 25% swelling agent.

It is understood that in order for the swelling plug to remain in the dry state, the humidity of the ambient air must remain less than 50%.

It will be observed that the proportion of 25% swelling agent is relatively low.

Albeit surprisingly, it was determined that the swelling dynamics of the swelling plug 15 are better (more rapid swelling) than with a much higher proportion by weight, such as 45%. This probably originates from the fact that with a higher proportion by weight there is a smaller exchange surface such that the liquid takes a longer time to reach the swelling agent.

Generally, it was determined that the swelling plug provides good swelling dynamics when the proportion of swelling agent is comprised between 20% and 30% by weight.

In practice, it is possible to find the content of swelling agent in the swelling plug 15 by weighing it in the dry state (as delivered in a straw in the empty state) then placing the swelling plug 15 in a water-permeable casing so that the threads remain grouped together, then washing the assembly in order to remove the swelling agent (which is virtually liquid in the dampened state and which is therefore removed by washing) then weighing the remaining threads in the dry state, which threads then comprise the fibrous support agent alone.

Here, the swelling plug 15 has a dry weight of the order of 1.07 mg per mm of length.

It has generally been determined that the swelling plug 15 performs very well when it has a weight comprised between 0.8 and 1.2 mg per mm of length.

The barrier plug 16 will now be described in detail, with reference to FIGS. 7 and 8.

The barrier plug 16 is a braid which is here formed by thirty-two identical threads arranged in a core 35 and a cover 36 surrounding the core 35.

The core 35 is formed by two threads arranged parallel, against one another.

The cover 36 has an annular cross section. It is formed by thirty braided threads divided into six strands each comprising two threads and six strands each comprising three threads.

One of the threads 37 which form the barrier plug 16 is shown very diagrammatically in cross-section in FIG. 8.

The thread 37 is formed from fibers 38 similar to the support fibers 33 of the thread 32 and by a coating 39 rendering the thread 37 hydrophobic.

Here, the coating 39 is of fluorinated resin.

Advantageously, the fluorinated resin is a fluorocarbon resin, for example having a formula $CF_3(CF_2)_n$ with n greater than 5 and preferably n=5 (C6 fluorinated resin) or n=7 (C7 fluorinated resin);

As a variant, the coating 39 to make the thread 37 hydrophobic is of polytetrafluoroethylene (PTFE).

Due to the fact that the threads 37 are rendered hydrophobic by the coating 39, the barrier plug 16 has a water-repellant effect.

This repellant effect does not prevent the substance 22 from passing through the barrier plug 16 and reaching the swelling plug 15, since in practice the substance 22 comes up against the stopper 12 with a certain speed.

During the passage of the substance 22 in the barrier plug 16, the threads 37 do not absorb liquid; and after the area 23 of constrained swelling of the swelling plug 15 is formed and the passage of the liquid-based substance is blocked, the barrier plug 16 does not keep the liquid situated in its interstices but returns it into the dose of liquid substance situated between the end 20 of the barrier plug 16 and the end 14 of the tube 11.

As a result, there is no consumption, or very reduced consumption, of liquid substance by the barrier plug 16.

The variant of the straw 10 shown in FIGS. 9 and 10 is similar to the straw 10 which has just been described with reference to FIGS. 1 to 8, except that:

the swelling plug 15 is shorter, here with a length (distance between its ends 17 and 18) which is of the order of 3 mm;

the tube 11 has a larger inner diameter, here of the order of 2.5 mm; and similarly, the swelling plug 15 and the barrier plug 16 have a larger diameter.

The outer diameter of the tube 11 is of the order of 3 mm.

Here, the swelling plug 15 of the straw 10 shown in FIGS. 9 and 10 is made with the same threads 32, but in greater numbers, than the swelling plug 15 of the straw 10 shown in FIGS. 1 to 4.

More precisely, as shown in FIG. 11, the swelling plug 15 of the straw 10 shown in FIGS. 9 and 10 is here a braid formed by forty-eight identical threads arranged in a core 30 formed by sixteen braided threads divided into twelve strands each comprising two threads and in a cover 31 with an annular cross section, surrounding the core 30, formed by twenty-four braided threads divided into twelve strands each comprising two threads.

Here, the barrier plug 16 is made with threads 37 that are similar to, but thicker than, the threads 37 of the barrier plug 16 of the straw 10 shown in FIGS. 1 to 4.

More precisely, as shown in FIG. 12, the barrier plug 16 of the straw 10 shown in FIGS. 9 and 10 is here a thread formed by twenty-eight identical threads arranged in a core 35 formed by four threads arranged parallel against one another, and in a cover 36 with an annular cross section and surrounding the core 35, formed by twenty-four threads divided into twelve strands each comprising two threads.

Due to the fact that the swelling plug 15 has a length (distance between its ends 17 and 18) which is of the order of 3 mm, the area 23 of constrained swelling, which here is also of the order of 3 mm, extends as shown in FIG. 10, over the entire length of the swelling plug 15.

A part of the swelling plug 15 that has come out of the tube 11 over a length of the order of 2 mm starting from the end 18, expands like the part 26 shown in FIG. 4.

Once the expansion is complete, the end 18 has a contour which has here a diameter d of the order of 6 mm.

Generally, by providing that the part of the swelling plug 15 which has come out of the tube 11 has a length l comprised between 2 and 3 mm, it is ensured that the part that has come out of the tube 11 belongs in its entirety to the area 23 of constrained swelling, which has a length of the order of 3 mm.

To observe the swelling, a part of the swelling plug 15 should be kept in the tube 11. For example, with the plug 15 of the straw 10 shown in FIGS. 1 and 4, the part that has come out of the tube may have a length l of 3 mm since the swelling plug 15 is longer. With the swelling plug 15 of the straw 10 shown in FIGS. 9 and 10, the part that has come out of the tube must have a length that is smaller than 3 mm (this is the length of the swelling plug 15).

It will be noted that the braiding of the threads 32 which form the swelling plug 15 allows the threads 32 to be held one against another, but that close to the ends the threads 32 can quite easily become unbraided and separated from one other.

The part of the swelling plug 15 that has come out of the tube, for the straw 10 shown in FIGS. 1 to 4 and equally for the straw 10 shown in FIGS. 9 and 10, is close to the end 18. The braiding of the threads 32 does not therefore prevent the yarns 32, or more specifically what is left after swelling of the swelling fibers 34, from coming away from each other.

In practice, generally, the end such as 18 of the part such as 23, having a length comprised between 2 mm and 3 mm starting from the end such as 18, expands with the end such as 18 adopting a diameter which can reach up to three times the inner diameter of the tube.

Generally, it was determined that the straw such as 10 performs very well when the part such as 23 of the swelling plug such as 15, that has a length comprised between 2 mm and 3 mm starting from the end such as 18, expands with the end such as 18 adopting a diameter at least equal to one and a half times the inner diameter of the tube.

For example, in the case of the straw 10 shown in FIGS. 1 to 4, the inner diameter of which is of the order of 1.6 mm, the diameter of the end 18 is at least equal to 2.4 mm; and in the case of the straw 10 shown in FIGS. 9 and 10, the inner diameter of which is of the order of 2.5 mm, the diameter of the end 18 is at least equal to 3.7 mm.

The swelling of the swelling agent is then suitably constrained by the tube 11.

In having its swelling thus constrained by the tube 11, the swelling agent of the swelling plug 15 becomes so compact that it blocks the passage of the liquid-based substance 22 while it confers mechanical strength on the area 23 of constrained swelling.

In particular, the swelling plug 15 retains its integrity (the swelling agent and the fibrous support agent are held against each other) when the swelling plug 15 is slid in the tube 11 in order to empty the straw 10.

It will be noted that the blocking of the liquid-based substance 22 achieved by the swelling plug 15, which takes place particularly rapidly as explained above, is particularly suitable for carrying out the filling of the straws 10 with an automatic machine, the operating speed of which may be very high, up to several thousand straws per hour.

In the straw 10 shown in FIGS. 9 and 10, the fact that the stopper is shorter makes it possible to maximize the space available for storage of the liquid-based substance.

It will be noted that in the straw 10 shown in FIGS. 1 to 4, the length of the stopper 12, i.e. the distance between the end 17 of the swelling plug 15 and the end 20 of the barrier plug 16 is of the order of 10 mm, and that the distance between the end 14 of the tube 11 and the end 17 of the swelling plug 15 is of the order of 7 mm.

The straw 10 shown in FIGS. 1 to 4 can therefore be used in exactly the same way as a conventional straw. In particular, in order to be emptied, it can be placed in a conventional insemination gun.

It will be observed that in the straw 10 shown in FIGS. 1 to 4, of which the inner diameter of the tube is of the order of 1.6 mm, and of which the inner cross section of the tube is therefore of the order of 2 $mm^2$, the swelling plug 15 comprises nineteen threads 32 i.e. 9.5 threads per $mm^2$ of cross-section of the tube; and that, in the straw 10 shown in FIGS. 9 and 10, of which the inner diameter of the tube is of the order of 2.5 mm, and of which the inner cross section of the tube is therefore of the order of 5 $mm^2$, the plug 15 comprises forty-eight threads i.e. 9.6 threads per $mm^2$ of cross section of the tube.

It has generally been determined that the swelling plug 15 performs very well when there are between 8 and 11 threads per $mm^2$ of cross section of the tube of the straw.

With the exception of the coating 39 of the threads 37, the barrier plug 16 of the straw 10 shown in FIGS. 1 to 4 and the barrier plug 16 of the straw 10 shown in FIGS. 9 and 10 are generally configured like one of the fibrous plugs of a conventional three-part stopper.

The variant of the straw 10 shown in FIG. 13 is similar to the straw 10 shown in FIGS. 1 to 4, except that the threads 32 which form the swelling plug 15, shown in FIG. 14, are similar to the thread 32 shown in FIG. 6 but comprise a coating 40 that changes hue between the dry state and the dampened state.

In the empty state, the swelling plug 15 of the straw 10 shown in FIG. 13 has the same appearance as the swelling plug 15 of the straw 10 shown in FIG. 1.

In the filled state, the area 23 of constrained swelling of the plug 15 of the straw shown in FIG. 13 has a different appearance to that of the plug 15 in the dry state.

More precisely, when the straw 10 shown in FIG. 13 is in the empty state, the swelling plug 15 has a first color and when this straw 10 is in the filled state shown in FIG. 13, the dampened part of the swelling plug 15 (area 23 of constrained swelling) has a second color.

Here, the hue of the first color (empty state) is brownish white while the hue of the second color (filled state) is greenish yellow.

For example, the swelling plug 15 when the straw is in the empty state, as viewed through the tube 11, has a Pantone® 155U color and the area 23 of the swelling plug 15 when the straw is in the filled state (FIG. 13), as viewed through the tube 11, has a Pantone® 395C color.

It is recalled here that the hue of a color corresponds to the wavelengths (or to the single wavelength in the case of a color of the rainbow) of the light emitted by the object having this color. The hue is only one of the components of the color, which depends on other parameters such as luminosity and saturation.

The change in hue of the swelling plug 15 between the dry state and the dampened state is due to the presence of the hue-change coating 40.

Here, the coating 40 is a fluorescein sodium salt.

It will be noted that the fluorescein sodium salt is not spermicidal and therefore is suitable for contact with animal semen.

It is known that the fluorescein sodium salt has the following formula:

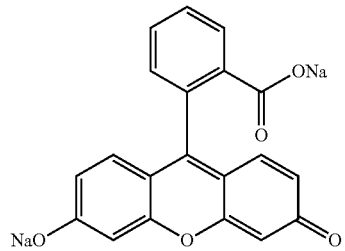

and that it is identified by the number CAS 518-47-8.

It is also known that the fluorescein sodium salt is a fluorophore salt i.e. capable of emitting fluorescent light when it is dissolved in water; while in the dry state it is a non-fluorophore salt.

When the swelling plug 15 of the straw 10 shown in FIG. 13 is in the dry state, the fluorescein sodium salt does not emit fluorescent light as it is in the dry state. When this swelling plug is in the dampened state, the fluorescein sodium salt is dissolved in the water contained in the portion 33 and then emits fluorescent light.

The change in hue of the portion 23 of the swelling plug 15 is due to the addition of fluorescent light.

By virtue of the presence of the fluorescein sodium salt, the swelling plug 15 forms an indicator component indicating contact between the stopper 12 and the substance 22: the plug for swelling 15 has a first predetermined color in the absence of prior contact with the substance 22 and a second predetermined color, having a different hue to the hue of the first color, when the swelling plug 15 has been in contact with the substance 22.

The component that is an indicator of contact with the substance 22, formed by the swelling plug 15, is useful for checking the correct filling of the straw 10, and more precisely the correct dampening of the stopper 12 by the substance 22.

Checking the correct filling of the straw can be carried out visually by the operator, simply by checking that the swelling plug 15 of the stopper 12 has adopted the hue of the second predetermined color, i.e. a greenish yellow hue in the present example.

The correct filling of the straw 10 can also be checked automatically.

In a variant of the swelling plug 15, the coating 40 of fluorescein sodium salt in the dry state is replaced by another product that is not fluorophore in the dry state and is fluorophore when it is dissolved in water, which is in the form of a salt in the dry state.

This is for example another fluorescein salt, a Rhodamine B salt, a Rhodamine 6G salt and/or a salt of Eriochrome® Cyanine R.

It is known that Rhodamine B has the following formula:

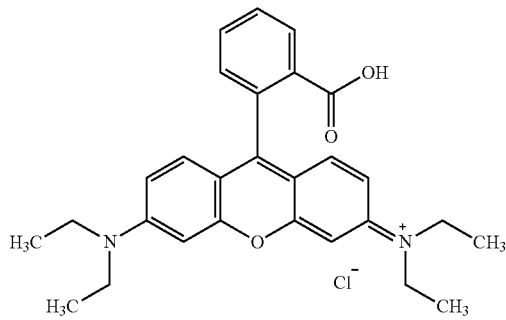 [SMILES: CCN(CC)c1ccc2c(-c3ccccc3C(=O)O)c3ccc(=[N+](CC)CC)cc-3oc2c1 ; [Cl-]]

and that it is identified by the number CAS 81-88-9.

It is known that Rhodamine 6G has the following formula:

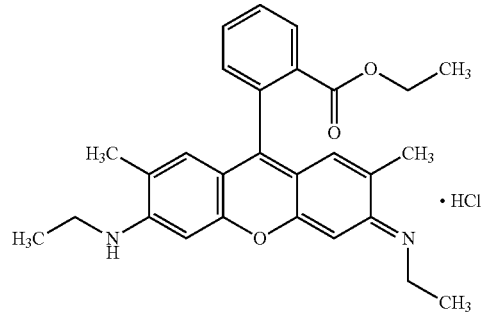 [SMILES: CC/N=c1\cc2oc3cc(NCC)c(C)cc3c(-c3ccccc3C(=O)OCC)c-2cc1C ; "· HCl"]

and that it is identified by the number CAS 989-38-8.

It is known that Eriochrome® Cyanine R has the following formula:

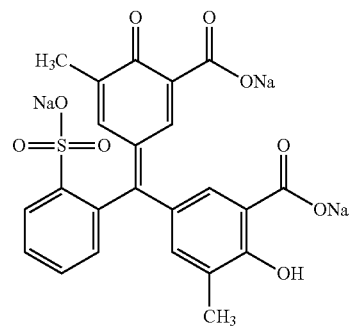

and that it is identified by the number CAS 64-18-9.

By selecting one or more of these products, the hue of the swelling plug 15 can be adjusted in the dampened state.

In other variants, the agent such as the coating 40 modifying the color of the swelling plug 15 is a colorant, without being fluorophore.

The color-modifying agent being a colorant, without being a fluorophore, is for example methylene blue or α-zurine.

Such colorant products, when they are in the dry state, have no effect, or only a slight effect, on the color of the other products forming the swelling plug 15. However, when the swelling plug 15 is dampened, the colorant product communicates its coloration to the rest of the swelling plug 15.

In other variants, the change in color of the swelling plug 15 is brought about on contact with a liquid other than water, for example a product contained in a diluent or a semen preservative for animal semen.

In other variants, the material of the tube such as 11 is not transparent, but translucent, for example slightly colored.

In variants that are not shown, the threads 32 of the swelling plug 15 are different from the threads shown in FIGS. 6 and 14, with for example the integration of the swelling agent being carried out by coating of fibers such as the support fibers 33, for example by soaking of threads made from such support fibers or by hot coating, or also by coextrusion of multi-filament support fibers and a single-filament swelling fiber, or also by close mixing of multifilament support fibers with a single-filament swelling fiber.

In other variants (not shown), the swelling plug 15 has different lengths, for example longer or shorter than the swelling plug 15 of the straw 10 shown in FIGS. 1 to 4.

In other variants (not shown), the stopper 12 is formed solely by the swelling plug 15 (there is no barrier plug 16).

In other variants (not shown), the threads such as 32 forming the swelling plug such as 15 are associated otherwise than by braiding, for example by stranding; and/or the support fibers 33 are made from a material other than polyester and/or viscose, for example polyamide or polypropylene.

The variant of the straw 10 shown in FIG. 15 is similar to the straw 10 shown in FIGS. 1 to 4, except that the swelling plug 15 is replaced by a powder 45 capable of transforming in contact with a liquid into an impermeable paste or gel adhering to the wall of the tube 11 in order for the stopper 12 to be liquid-tight, and by a plug 46 of a fibrous substance.

Thus, the stopper 12 of the straw 10 illustrated in FIG. 15 is of the three-part type, with the barrier plug 16 and the fibrous plug 46 enclosing the powder 45.

The stopper 12 is similar to the conventional three-part stoppers, except that the barrier plug 16 is formed over the whole cross-section of the tube 11 by threads 37 each comprising fibers 38 and a coating 39 in order for the threads 37 to be hydrophobic.

In a variant not illustrated, the threads 37 are hydrophobic by nature, for example because they are of fluorine.

In a variant not illustrated, the stopper such as 12 comprises, in addition to the barrier plug 16, a liquid-tight gas-permeable sealing component different from the swelling plug 15 and from the assembly formed by the powder 45 and by the fibrous plug 46, for example a one-piece cylinder of hydrophobic microporous material as described in European patent application EP 0 873 726 or a one-piece cylinder of sintered self-sealing microporous material as described in PCT application WO 2010/070533.

In the examples described and illustrated, the barrier plug 16 is the only component of the stopper 12 between the sealing component such as the swelling plug 15 or the assembly formed by the powder 45 and the fibrous plug 46 and the location at which the liquid-based substance such as 22 is to be located. As a variant, there is also another component of the stopper 12, for example an identification component such as a magnetic thread.

In all the examples described and illustrated, there is nothing other than the sealing component (swelling plug 15 or assembly formed by the powder 45 and the fibrous plug 46) between the barrier plug 16 and the end of the stopper 12 closest to the neighboring end of the tube 11. As a variant, the stopper 12 comprises other components, for example an identification component such as a magnetic thread.

Numerous other variants are possible according to circumstances, and in this connection it is to be noted that the invention is not limited to the examples described and shown.

The invention claimed is:

1. A straw for preservation of a predetermined dose of liquid-based substance containing water, comprising a tube configured to be filled with the liquid-based substance, the liquid-based substance being a biological substance, the tube extending between a first end and a second end and further comprising a liquid-tight, gas-permeable stopper, the stopper being disposed in the tube close to a first end of the tube and extending between a first end turned towards the first end of the tube and a second end turned towards the second end of the tube, said stopper and said tube being configured so that after the liquid-based substance has come to meet the stopper by the second end of the stopper, the stopper blocks passage of the liquid-based substance and, by pushing on the first end of the stopper, the stopper is slidable in the tube towards the second end of the tube;

wherein the stopper comprises towards the second end of the tube a barrier plug formed over the whole cross-section of the tube by hydrophobic threads, the barrier plug being configured to allow the liquid-based biological substance to pass therethrough while filling the tube but to be repelled by the barrier plug while passage of the liquid-based substance is blocked by the stopper.

2. The straw according to claim 1, wherein each thread comprises fibers and a coating to make the thread hydrophobic, which coating comprises a fluorinated resin.

3. The straw according to claim 2, wherein said fluorinated resin is a fluorocarbon resin.

4. The straw according to claim 2, wherein said coating is polytetrafluoroethylene (PTFE).

5. The straw according to claim 1, wherein said stopper comprises, in addition to said barrier plug, a liquid-tight gas-permeable sealing component, with a first end of the barrier plug, turned towards the first end of the tube, and a second end of the sealing component, turned towards the second end of the tube, the first end of the barrier plug and the second end of the sealing component being disposed against each other.

6. The straw according to claim 5, wherein said sealing component is a swelling plug comprising a fibrous support agent and a swelling agent, the swelling agent being associated with the support agent, that swells by absorption of water in contact with the liquid-based substance.

7. The straw according to claim 6, wherein said barrier plug extends between said first end of the barrier plug and a second end forming the second end of the stopper.

8. The straw according to claim 6, wherein said swelling plug extends between a first end forming the first end of the stopper and said second end of the sealing component.

9. The straw according to claim 6, wherein the barrier plug is a braid formed by associating threads and the swelling plug is a braid formed by associating threads, the barrier plug comprising more threads than the swelling plug.

10. The straw according to claim 6, wherein the swelling agent is a superabsorbent polymer configured to absorb water in a volume several hundred times a volume of the superabsorbent polymer.

11. The straw according to claim 6, wherein the swelling agent is sodium polyacrylate.

12. The straw according to claim 5, wherein the sealing component has a first predetermined color in absence of prior contact with the liquid-based substance and a second predetermined color, having a hue different from a hue of the first color, when the sealing component has been in contact with said substance.

13. The straw according to claim 12, wherein said sealing component comprises a salt that is non-fluorophore in a dry state and fluorophore when the salt is dissolved in water.

14. The straw according to claim 13, wherein said salt forms part of the group comprising a fluorescein salt, a Rhodamine B salt, a Rhodamine 6G salt and a salt of Eriochrome® Cyanine R.

15. A straw for preservation of a predetermined dose of liquid-based substance containing water, comprising a tube configured to be filled with the liquid-based substance, the liquid-based substance being a biological substance, the tube extending between a first end and a second end and further comprising a liquid-tight, gas-permeable stopper, the stopper being disposed in the tube close to a first end of the tube and extending between a first end turned towards the first end of the tube and a second end turned towards the second end of the tube, said stopper and said tube being configured so that after the liquid-based substance has come to meet the stopper by the second end of the stopper, the stopper blocks passage of the liquid-based substance and, by pushing on the first end of the stopper, the stopper is slidable in the tube towards the second end of the tube;

wherein the stopper comprises towards the second end of the tube a barrier plug formed over the whole cross-section of the tube by hydrophobic threads, wherein each thread comprises fibers and a coating to make the thread hydrophobic, which coating comprises a fluorinated resin, wherein said fluorinated resin is a fluorocarbon resin, and wherein said fluorocarbon resin has a formula $CF_3(CF_2)_n$ with n greater than or equal to 5 and selected so that the fluorocarbon resin is hydrophobic.

* * * * *